United States Patent [19]
Finkam et al.

[11] Patent Number: 5,852,216
[45] Date of Patent: Dec. 22, 1998

[54] PREPARATION AND USE OF (3-ALKOXY-PHENYL) MAGNESIUM CHLORIDES

[75] Inventors: Michael Finkam, Aachen; Thomas Kohnen, Stolberg; Werner Winter, Aachen, all of Germany

[73] Assignee: Gruenenthal GmbH, Aachen, Germany

[21] Appl. No.: 800,879

[22] Filed: Feb. 14, 1997

[30] Foreign Application Priority Data

Feb. 16, 1996 [DE] Germany .................. 196 05 778.7

[51] Int. Cl.$^6$ .................................. C07C 215/00
[52] U.S. Cl. .................... 564/443; 260/665 G; 568/630; 568/631
[58] Field of Search .............. 260/665 G; 564/443; 568/630, 631

[56] References Cited

U.S. PATENT DOCUMENTS

| | | | |
|---|---|---|---|
| 2,959,596 | 11/1960 | Ramsden et al. | |
| 3,706,809 | 12/1972 | Moroe et al. | 260/665 G |
| 4,133,824 | 1/1979 | Malpass et al. | 260/665 G X |
| 4,731,203 | 3/1988 | Bogdanovic | 260/665 G |
| 5,273,686 | 12/1993 | Bogdanovic et al. | 260/665 G X |
| 5,358,670 | 10/1994 | Turnbull et al. | 260/665 G |

FOREIGN PATENT DOCUMENTS

| | | |
|---|---|---|
| 307106 | 3/1989 | European Pat. Off. |
| 60-72833 | 4/1985 | Japan |

OTHER PUBLICATIONS

Bhattacharya et al., "Preparation of Arenesulphonyl Chlorides from Grignard Reagents", *J. Chem. Soc.*, (C) 1968, pp. 1265–1267.

Rieke et al., "Activated Metals. IV. Preparation and Reactions of Highly Reactive Magnesium Metal", *Journal of the American Chemical Society*, 96:6, (1974), pp. 1775–1781.

Burns et al., "Highly Reactive Magnesium and Its Application to Organic Syntheses", *J. Org. Chem.*, vol. 52 (1987), pp. 3674–3680.

Flick et al., "Untersuchungen zur chemischen Struktur und analgetischen Wirkung von phenylsubstitutierten Aminomethylcyclohexanolen", *Arzneim.—Forsch./Drug Res.*, vol. 28 (I), (1978), pp. 107–113.

*Primary Examiner*—Paul F. Shaver
*Attorney, Agent, or Firm*—Evenson, McKeown, Edwards & Lenahan, P.L.L.C.

[57] ABSTRACT

A method of preparing (3-alkoxyphenyl)magnesium chlorides and the use thereof for reaction with certain carbonyl compounds are described.

5 Claims, No Drawings

PREPARATION AND USE OF (3-ALKOXY-PHENYL) MAGNESIUM CHLORIDES

This invention relates to a method of preparing (3-alkoxyphenyl)magnesium chlorides and to the use of these compounds.

Numerous pharmaceutical and agrochemical active ingredients contain the m-anisyl group. This is preferably introduced into the compound to be synthesised by means of an organometallic m-anisyl compound, particularly by means of an m-anisyl Grignard compound. m-anisylmagnesium bromide, which is obtained by the reaction of m-anisyl bromide with metallic magnesium in a solvent, is used as the Grignard compound here (Arzn. Forsch./Drug Res. 28 (I), 107 (1978)).

The reactive bromides are usually employed for the preparation of Grignard compounds. From an economic and ecological point of view, however, the replacement of bromides by the less reactive chlorides in the preparation of Grignard reagents has advantages, since chlorides are firstly less expensive and secondly give rise to smaller amounts of salts on account of their lower molecular weights. Moreover, fewer by-products are formed when chlorides are used.

The preparation and use of o- and p-anisylmagnesium chloride is known from U.S. Pat. No. 2,959,596 and J. Chem. Soc. 1968, 1265. JP 60/72833, which is referred to in Derwent WPI Acc No: 85-137805/23, discloses (4-ethoxyphenyl)magnesium chloride without stating the method of preparation used. However, the preparation and use of (3-methoxyphenyl)- and (3-ethoxyphenyl) magnesium chloride have not been described hitherto. This can be explained by the electron deactivation of the aromatic compound by the alkoxy group in the meta position.

The underlying object of the present invention therefore consisted of developing a method of preparing (3-alkoxyphenyl)magnesium chlorides.

It has surprisingly been found that (3-alkoxyphenyl) magnesium chlorides containing one to five carbon atoms in their alkoxy radical can be obtained in high yields by the reaction of the corresponding 3-alkoxyphenyl chlorides with activated magnesium.

Accordingly, the present invention relates to a method of preparing (3-alkoxyphenyl)magnesium chlorides containing one to five carbon atoms in their alkoxy radical, which are prepared by the reaction of a (3-alkoxyphenyl) chloride with activated magnesium which is obtained by the reduction of magnesium halides with an alkali metal.

Activated magnesium which is particularly suitable for the method according to the invention is that which is obtained by the reduction of magnesium halides, particularly magnesium chloride, with lithium, sodium or potassium (J. Org. Chem. 52, 3674, (1987); J. Am. Chem. Soc. 96, 1775 (1974)). Reduction is usually effected with a 1 to 5% molar excess of magnesium halide in a solvent or solvent mixture, for example in aliphatic ethers such as tetrahydrofuran, substituted tetrahydrofurans, dimethoxyethane and/or dimethyl diglycol, at temperatures between 65° C. and 162° C. It may be advantageous to conduct the reaction in the presence of alkali and alkaline earth metal salts, for example alkali iodides, alkali sulphates and/or alkaline earth metal sulphates. The activated magnesium which is obtained by reduction is preferably reacted, without being isolated, with a 3-alkoxyphenyl chloride containing one to five carbon atoms in its alkoxy radical to form the corresponding Grignard compound. The $C_{1-5}$ alkoxy radical in the phenyl chloride compound may be a straight chain, branched or cyclo radical. Phenyl chloride compounds are preferred which contain a meta alkoxy radical and which are selected from the group comprising methoxy, ethoxy, propoxy, isopropoxy, n-butoxy and cyclopentoxy. 3-methoxyphenyl chloride and 3-ethoxyphenyl chloride are particularly preferred for the reaction with activated magnesium.

The magnesium chloride compounds can be prepared in high yields and without the formation of by-products by the method according to the invention. In contrast, if 3-alkoxyphenyl chlorides are reacted with magnesium which is not activated and in the presence of small amounts of dibromoethane, or with magnesium which is not activated and in the presence of ethyl bromide by the method for 3-t-butoxyphenyl chloride which is described in EP 307 106, the corresponding Grignard compounds are only obtained in unsatisfactory yields. Moreover, the formation of by-products occurs to a considerable extent.

Aldehydes and ketones can be converted in high yields into the corresponding alcohols with the (3-alkoxyphenyl) magnesium chlorides prepared according to the invention.

Therefore, the present invention also relates to the use of a (3-alkoxyphenyl)magnesium chloride containing one to five carbon atoms in its alkoxy radical for reaction with a β-aminoaldehyde or β-aminoketone of formula I

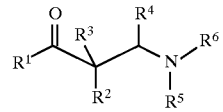

where $R^1$ represents H or a $C_{1-4}$ alkyl, $R^2$ represents H or a $C_{1-4}$ alkyl, or $R^2$ together with $R^1$ represents —$(CH_2)_4$—, or $R^2$ together with $R^3$ represents a $C_{4-7}$ cycloalkyl, or $R^2$ together with $R^4$ represents a $C_{5-8}$ cycloalkyl, or $R^2$ together with $R^5$ represents a five- to eight-membered heterocycle and $R^3$ constitutes H or a straight chain $C_{1-4}$ alkyl, $R^4$ is H, and $R^5$ represents a $C_{1-3}$ alkyl and $R^6$ represents a $C_{1-3}$ alkyl, or for reaction with an aldehyde or ketone of formula II

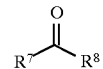

where $R^7$ and $R^8$ are the same or different and each represent H, a $C_{1-6}$ alkyl or a $C_{3-6}$ cycloalkyl.

A (3-alkoxyphenyl)magnesium chloride in which the alkoxy radical represents methoxy, ethoxy, propoxy, isopropoxy, n-butoxy or cyclopentoxy is preferably used for reaction with a β-aminoaldehyde or with a β-aminoketone. (3-methoxyphenyl)magnesium chloride or (3-ethoxyphenyl) magnesium chloride is most preferably used. β-aminoaldehydes or β-aminoketones which are particularly suitable are those of formula I in which $R^1$ is a $C_{1-4}$ alkyl, $R^2$ represents H or a $C_{1-4}$ alkyl, or $R^2$ together with $R^1$ represents —$(CH_2)_4$—, $R^3$ represents H or a straight chain $C_{1-4}$ alkyl, and $R^4$ constitutes H, $R^5$ constitutes $CH_3$ and $R^6$ constitutes $CH_3$.

The reaction of a magnesium chloride compound prepared according to the invention is effected in the manner known in the art, in that the Grignard compound is reacted with a compound of formula I or II in a solvent or solvent mixture, for example in aliphatic ethers such as tetrahydrofuran, substituted tetrahydrofurans, dialkyl ethers and/or dioxane, and/or aromatic hydrocarbons such as benzene, toluene and/or xylene, at temperatures between −78° C. and 120° C.

EXAMPLES

All work was carried out with dried solvents and reagents under a protective gas atmosphere.

Example 1

Preparation of (3-methoxyphenyl)magnesium chloride 2.04 g (21.4 mmole) magnesium chloride were placed in a 100 ml three-necked flask fitted with a reflux condenser, thermometer and dropping funnel and were covered with 50 ml tetrahydrofuran (THF). 0.82 g (21.0 mmole) of freshly cut potassium was added in portions and the mixture was heated under reflux for 90 minutes, with stirring. Thereafter, 3.05 g (21.4 mmole) 3-chloroanisole, dissolved in 20 ml THF, was added drop-wise with stirring over 30 minutes. After the addition was complete, the mixture was stirred for 20 hours at room temperature and the Grignard compound obtained was used for further reaction.

Example 2

Preparation of 2-((dimethylamino)methyl)-1-(3-methoxyphenyl)-cyclohexanol 3.32 g (21.4 mmole) of 2-(dimethylamino)methyl-cyclohexanone, dissolved in 10 ml THF, were added drop-wise over 40 minutes to the solution of (3-methoxyphenyl) magnesium chloride obtained according to Example 1, whilst the latter was cooled in an ice bath. After stirring for 24 hours at room temperature, the mixture was hydrolysed with 20 ml of 20% ammonium chloride solution whilst being cooled in an ice bath. The organic phase was separated off and the aqueous phase was extracted twice more with ethyl acetate. The combined organic phases were dried over magnesium sulphate and filtered. After removing the solvent by distillation, 3.4 g (60% theoretical) of the cyclohexanol compound were obtained.

What is claimed is:

1. A method comprising reacting a (3-alkoxyphenyl)magnesium chloride wherein the alkoxy group contains one to five carbon atoms with a β-aminoaldehyde or β-aminoketone corresponding to formula I

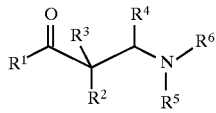

wherein $R^1$ represents H or $C_{1-4}$ alkyl;

$R^2$ represents H or $C_{1-4}$ alkyl, or
    $R^2$ together with $R^1$ represents —$(CH)_4$—, or
    $R^2$ together with $R^3$ represents a $C_{4-7}$ cycloalkyl, or
    $R^2$ together with $R^4$ represents a $C_{5-8}$ cycloalkyl, or
    $R^2$ together with $R^5$ represents a five- to eight-membered heterocycle;

$R^3$ represents H or straight chain $C_{1-4}$ alkyl;

$R^4$ represents H;

$R^5$ represents $C_{1-3}$ alkyl, and $R^6$ represents $C_{1-3}$ alkyl; or with an aldehyde or ketone corresponding to formula II

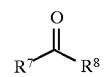

wherein $R^7$ and $R^8$ are the same or different and each represent H, $C_{1-6}$ alkyl or $C_{3-6}$ cycloalkyl.

2. A method according to claim 1, wherein a (3-alkoxyphenyl)magnesium chloride is reacted with a β-aminoaldehyde or β-aminoketone.

3. A method according to claim 1, wherein a (3-alkoxyphenyl)magnesium chloride is reacted with a β-aminoaldehyde or with a β-aminoketone corresponding to formula I, wherein $R^1$ represents $C_{1-4}$ alkyl, $R^2$ represents H or $C_{1-4}$ alkyl, or $R^2$ together with $R^1$ represents —$(CH_2)_4$—, $R^3$ represents H or straight chain $C_{1-4}$ alkyl, $R^4$ represents H, $R^5$ represents $CH_3$, and $R^6$ represents $CH_3$.

4. A method according to claim 1, wherein the alkoxy group in the (3-alkoxyphenyl)magnesium chloride is selected from methoxy, ethoxy, propoxy, isopropoxy, n-butoxy and cyclopentoxy.

5. A method according to claim 1, wherein the (3-alkoxyphenyl)magnesium chloride is (3-methoxyphenyl) magnesium chloride or (3-ethoxyphenyl)magnesium chloride.

* * * * *